(12) United States Patent
Gildor et al.

(10) Patent No.: US 11,639,933 B2
(45) Date of Patent: May 2, 2023

(54) DIGITAL AFFINITY LINKAGE ASSAY

(71) Applicant: Bio-Rad Laboratories, Inc., Hercules, CA (US)

(72) Inventors: Boaz Gildor, Haifa (IL); Dalia Shezifi, Kibutz Nahsholim (IL)

(73) Assignee: Bio-Rad Laboratories, Inc., Hercules, CA (US)

( * ) Notice: Subject to any disclaimer, the term of this patent is extended or adjusted under 35 U.S.C. 154(b) by 1111 days.

(21) Appl. No.: 16/141,069

(22) Filed: Sep. 25, 2018

(65) Prior Publication Data

US 2019/0094214 A1    Mar. 28, 2019

Related U.S. Application Data

(60) Provisional application No. 62/564,029, filed on Sep. 27, 2017.

(51) Int. Cl.
*G01N 33/543* (2006.01)
*G01N 33/541* (2006.01)

(52) U.S. Cl.
CPC ..... *G01N 33/54386* (2013.01); *G01N 33/541* (2013.01); *G01N 33/54306* (2013.01)

(58) Field of Classification Search
None
See application file for complete search history.

(56) References Cited

U.S. PATENT DOCUMENTS

| | | | |
|---|---|---|---|
| 9,850,515 B2 | 12/2017 | McCoy et al. | |
| 9,896,717 B2 | 2/2018 | Hodges et al. | |
| 2010/0022414 A1* | 1/2010 | Link | G01N 15/1459 506/18 |
| 2012/0122714 A1 | 5/2012 | Samuels et al. | |
| 2012/0329664 A1 | 12/2012 | Saxonov et al. | |
| 2014/0228239 A1 | 8/2014 | McCoy et al. | |
| 2014/0336068 A1 | 11/2014 | Hodges et al. | |
| 2015/0132743 A1 | 5/2015 | Egidio et al. | |
| 2017/0009274 A1* | 1/2017 | Abate | C12N 15/1096 |
| 2017/0160292 A1* | 6/2017 | Wilson | G01N 33/54306 |

FOREIGN PATENT DOCUMENTS

WO    2014/182835 A1    11/2014

OTHER PUBLICATIONS

Dhillon, H.S. et al.; "Homogeneous and digital proximity ligation assays for the detection of Clostridiuim difficile toxins A and B"; *Biomolecular Detection and Quantification*; vol. 10, Dec. 1, 2016; pp. 2-8.
Darmanis, S. et al.; "Sensitive Plasma Protein Analysis by Microparticle-based Proximity Ligation Assays"; *Molecular & Cellular Proteomics*; vol. 9, No. 2; Feb. 1, 2010; pp. 327-335.
Greenwood, C. et al.; "Proximity assays for sensitive quantification of proteins"; *Biomolecular Detection and Quantification*; vol. 4; Jun. 1, 2015; pp. 10-16.
Schroeder, H. et al.; "Immuno-PCR with digital readout"; *Biochemical and Biophysical Research Communications*; Elsevier, Amsterdam NL; vol. 488, No. 2; May 5, 2017; pp. 311-315.
Extended European Search Report from EP Appln. 18861806.0 dated Apr. 14, 2021; 11 pages.
International Search Report and Written Opinion from PCT Application PCT/US2018/052588 dated Jan. 28, 2019; 16 pages.
Safarik I. et al.; "Magnetic techniques for the isolation and purification of proteins and peptides"; *BioMaqnetic Research and Technology*; vol. 2, No. 7; Nov. 26, 2004; 17 pages.
NANOCS; "Fluorescent Streptavidin Silica Particle"; retrieved from the internet https://www.google.com/search?q=nanocs+fluorescent+streptavidin-silica+beads&source=Int&tbs=cdr%3A1%2Ccd_min%3A%sCcd_max%3A9%2F26%sF2017&tbm=; Feb. 11, 2016 2 pages.

* cited by examiner

*Primary Examiner* — Ann Montgomery
(74) *Attorney, Agent, or Firm* — Kilpatrick Townsend and Stockton LLP

(57) ABSTRACT

Methods of detecting a target in a sample are provided. Kits for performing the methods described herein are also provided.

15 Claims, 6 Drawing Sheets

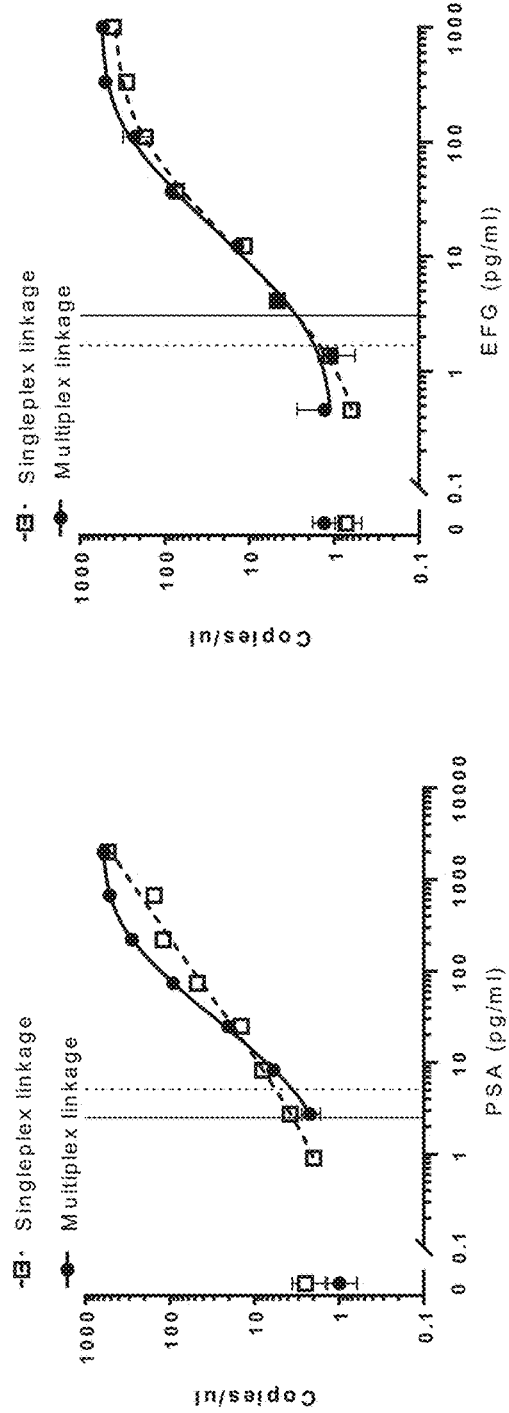
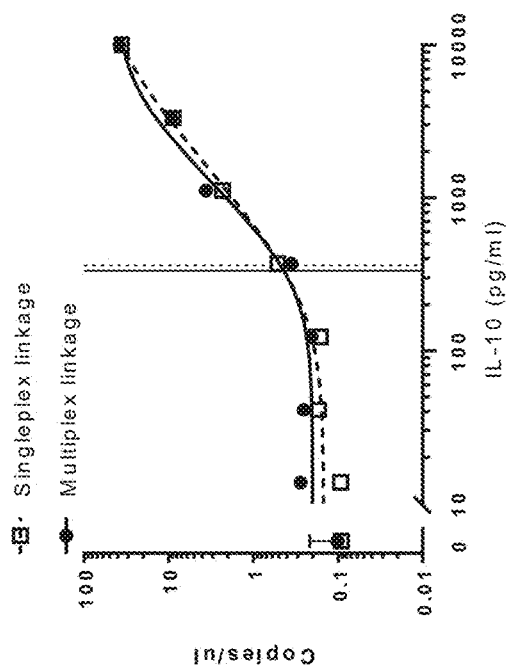
FIG. 6A
FIG. 6B
FIG. 6C

DIGITAL AFFINITY LINKAGE ASSAY

This application claims the benefit of U.S. Provisional Application 62/564,029 filed on Sep. 27, 2017 which is hereby incorporated by reference in its entirety.

BACKGROUND

Quantifying the amount of biomolecules in a sample from a subject can provide useful information for a number of clinical applications. One method for detecting and quantifying biomolecules, such as proteins, is by enzyme-linked immunosorbent assay (ELISA). However, the limit of detection and precision of quantification with this assay are not sufficient for many needs. Alternative techniques such as immuno-PCR have the potential to increase the sensitivity of detection, but in practice are limited by the problem of high background signal due to non-specific binding of the antibodies used as detection agents.

SUMMARY

Disclosed herein are methods, compositions, and kits for detecting a target in a sample.

In an embodiment, a method of detecting a target in a sample comprises contacting the sample with a first affinity agent linked to a solid support, wherein the first affinity agent specifically binds to the target, if present, thereby forming a target bound to the first affinity agent; separating the target bound to the first affinity agent from unbound material in the sample based on the presence or absence of the solid support, thereby generating a separated sample comprising the target bound to the first affinity agent; contacting the separated sample with a second affinity agent comprising a first label and a third affinity agent comprising a second label, wherein the second and third affinity agents specifically bind to the target, thereby forming a target-labeled affinity agent complex; separating the target-labeled affinity agent complex from uncomplexed second and third affinity agents based on the presence or absence of the solid support, thereby generating a separated target-labeled affinity agent complex; partitioning at least the separated target-labeled affinity agent complex into a plurality of partitions; and detecting the presence of the target in the sample by detecting the presence of the first and second labels in at least one same partition.

In some embodiments, the method of detecting a target in a sample comprises contacting the sample with a first affinity agent linked to a solid support, a second affinity agent comprising a first label, and a third affinity agent comprising a second label, wherein the first, second and third affinity agents specifically bind to the target, if present, thereby forming a target-labeled affinity agent complex; separating the target-labeled affinity agent complex from uncomplexed components in the sample based on the presence or absence of the solid support, thereby generating a separated target-labeled affinity agent complex; partitioning at least the separated target-labeled affinity agent complex into a plurality of partitions; and detecting the presence of the target in the sample by detecting the presence of the first and second labels in at least one same partition.

In certain embodiments, the method of detecting a target in a sample comprises contacting the sample with a second affinity agent comprising a first label and a third affinity agent comprising a second label, wherein the second and third affinity agents specifically bind to the target, if present, thereby forming a first complex comprising the target, the second affinity agent and third affinity agent; contacting the first complex with a first affinity agent linked to a solid support, wherein the first affinity agent specifically binds to the target, thereby forming a target-labeled affinity agent complex comprising the target, the first affinity agent, the second affinity agent, and the third affinity agent; separating the target-labeled affinity agent complex from uncomplexed components based on the presence or absence of the solid support, thereby generating a separated target-labeled affinity agent complex; partitioning at least the separated target-labeled affinity agent complex into a plurality of partitions; and detecting the presence of the target in the sample by detecting the presence of the first and second labels in at least one same partition.

In some embodiments, the method of detecting a target in a sample comprises conjugating a plurality of solid supports to a plurality of proteins in the sample comprising the target, if present, thereby forming a plurality of solid support conjugates, wherein the target comprises at least one of the plurality of proteins; separating the plurality of solid support conjugates from unconjugated material in the sample based on the presence or absence of the plurality of solid supports, thereby generating a separated plurality of solid support conjugates; contacting the separated plurality of solid support conjugates with a first affinity agent comprising a first label and a second affinity agent comprising a second label, wherein the first and second affinity agents specifically bind to the target, thereby forming a target-labeled affinity agent complex; separating the target-labeled affinity agent complex from uncomplexed first and second affinity agents based on the presence or absence of the solid support, thereby generating a separated target-labeled affinity agent complex; partitioning at least the separated target-labeled affinity agent complex into a plurality of partitions; and detecting the presence of the target in the sample by detecting the presence of the first and second labels in at least one same partition. In some embodiments, the conjugating comprises cross-linking.

In some embodiments, the first affinity agent is cleaved from the solid support prior to the partitioning step, thereby releasing the target-labeled affinity agent complex from the solid support. In some embodiments, an amino acid tag linking the first affinity agent to the solid support is cleaved by a sequence-specific protease. In certain embodiments, the protease is TEV, factor Xa, or thrombin. In some embodiments, a photo-cleavable linker between the solid surface and the first affinity agent is cleaved by exposing the linker to light.

In some embodiments, the target-labeled affinity agent complex is cross-linked prior to partitioning the separated target-labeled affinity agent complex into a plurality of partitions.

In some embodiments, the first label is a first nucleic acid label and the second label is a second nucleic acid label. In certain embodiments, the first and second nucleic acid labels are amplified following the partitioning. In some embodiments, each of the first and second nucleic acid labels are detected using a DNA probe (e.g., a TAQMAN™ probe, a SCORPION™ probe, an ECLIPSE™ probe, a molecular beacon probe, a double-stranded probe, a dual hybridization probe, or a double-quenched probe). In certain embodiments, each of the first and second nucleic acid labels are detected using an intercalating dye (e.g., EvaGreen® dye. In some embodiments, the first and second nucleic acid labels are detected using different signal levels of the same DNA probe or intercalating dye. In some embodiments, the first label is a first fluorophore and the second label is a second fluorophore. In certain embodiments, the first label is a first enzyme, the second label is a second enzyme, and the detecting comprises detecting products generated by the first and second enzymes. In some embodiments, the first label generates a first signal and the second label generates a second signal and the first signal and the second signal are distinguishable.

In some embodiments, the first label and the second label are each linked to streptavidin, the second and third affinity agents are biotinylated, and the second and third affinity agents are labeled with the streptavidin-linked first and second labels, respectively, prior to a first step of the method by allowing the first and second labeled streptavidins to bind to the respective biotinylated second and third affinity agents (i.e., by streptavidin-biotin interaction).

In some embodiments, the first affinity agent is biotinylated and the solid support is linked to streptavidin, and prior to a first step of the method the streptavidin-linked solid support is linked to the first affinity agent by allowing the streptavidin-linked solid support to bind to the biotinylated first affinity agent (i.e., by streptavidin-biotin interaction).

In certain embodiments, the solid support or the plurality of solid supports is/are a magnetic bead(s), a non-magnetic bead(s), or a surface(s) of a reaction vessel(s). In some embodiments, the non-magnetic beads are polystyrene beads or silica-based beads. In some embodiments, the solid support or the plurality of solid supports are magnetic beads and the target-labeled affinity agent complex is separated from the uncomplexed components in the sample using a magnet that attracts the magnetic beads linked to the first affinity agent in the target-labeled affinity agent complex. In certain embodiments, the solid support or the plurality of solid supports are non-magnetic beads and the target-labeled affinity agent complex is separated from the uncomplexed components in the sample by centrifugation. In some embodiments, the solid support is a surface of a reaction, and the target-labeled affinity agent complex is separated from the uncomplexed components in the sample by aspiration.

In certain embodiments, the target comprises a protein, a protein aggregate, or a protein oligomer. In some embodiments, the target is a complex of two or more interacting proteins and the second and third affinity agents each bind to one of the interacting proteins in the complex. In some embodiments, the target has a repeating identical epitope and the first and second affinity agents or the first and third affinity agents recognize the same epitope. In some embodiments, two or more of the first, second, and third affinity agents recognize a different epitope on the target. In some embodiments, each of the first, second, and third affinity agents recognizes a different epitope on the target.

In some embodiments, the first, second, and third affinity agents are each selected from the group consisting of an antibody, an antibody fragment, and a nucleotide aptamer. In some embodiments, the antibody is a monoclonal antibody and/or a polyclonal antibody.

In some embodiments (e.g., a multiplexing embodiment), the target is a plurality of different targets, the first affinity agent is a plurality of different first affinity agents, the second affinity agent is a plurality of different second affinity agents comprising a plurality of first labels, and the third affinity agent is a plurality of different third affinity agents comprising a plurality of second labels and wherein a set of the first, second and third affinity agents specifically bind to the same one of the plurality of different targets.

In certain embodiments, the method further comprises determining the number of partitions comprising the first label and the second label, thereby quantifying the target. In some embodiments, the partitions are droplets.

In an embodiment, a kit for detecting a target in a sample comprises a first affinity agent linked to a solid support; a second affinity agent comprising a first label; and a third affinity agent comprising a second label, wherein each of the first, second, and third affinity agents specifically binds to the target. In some embodiments, the second and third affinity agents specifically bind to different epitopes on the target than the first affinity agent. In some embodiments, a kit for detecting a target in a sample comprises a chemically modified solid support; a first label; and a second label, wherein each of first and second labels is linked to streptavidin.

In some embodiments in which the first label is a first oligonucleotide and the second label is a second oligonucleotide, the kit further comprises a DNA polymerase, PCR primers, PCR probes, dNTPs, a buffer, and/or a PCR master mix. In some embodiments in which the first label is a first enzyme and the second label is a second enzyme, the kit further comprises at least one of a first and second substrate for the respective first and second enzymes, and/or a buffer. In certain embodiments, the kit further comprises instructions for performing a method of detecting a target in a sample.

BRIEF DESCRIPTION OF THE DRAWINGS

FIGS. 6A-6C show intra-assay comparison of dose response curves for experiments as described in Examples 2 and 3, quantitation of different target proteins using either singleplex or multiplex linkage assays. For each target protein, the results from a singleplex assay (square markers with dashed curves) were compared to multiplex assay (circle markers with solid curve). The vertical lines mark the calculated LOD values for the singleplex assays vs. the multiplex assays.

DETAILED DESCRIPTION

I. Introduction

Figure 1:
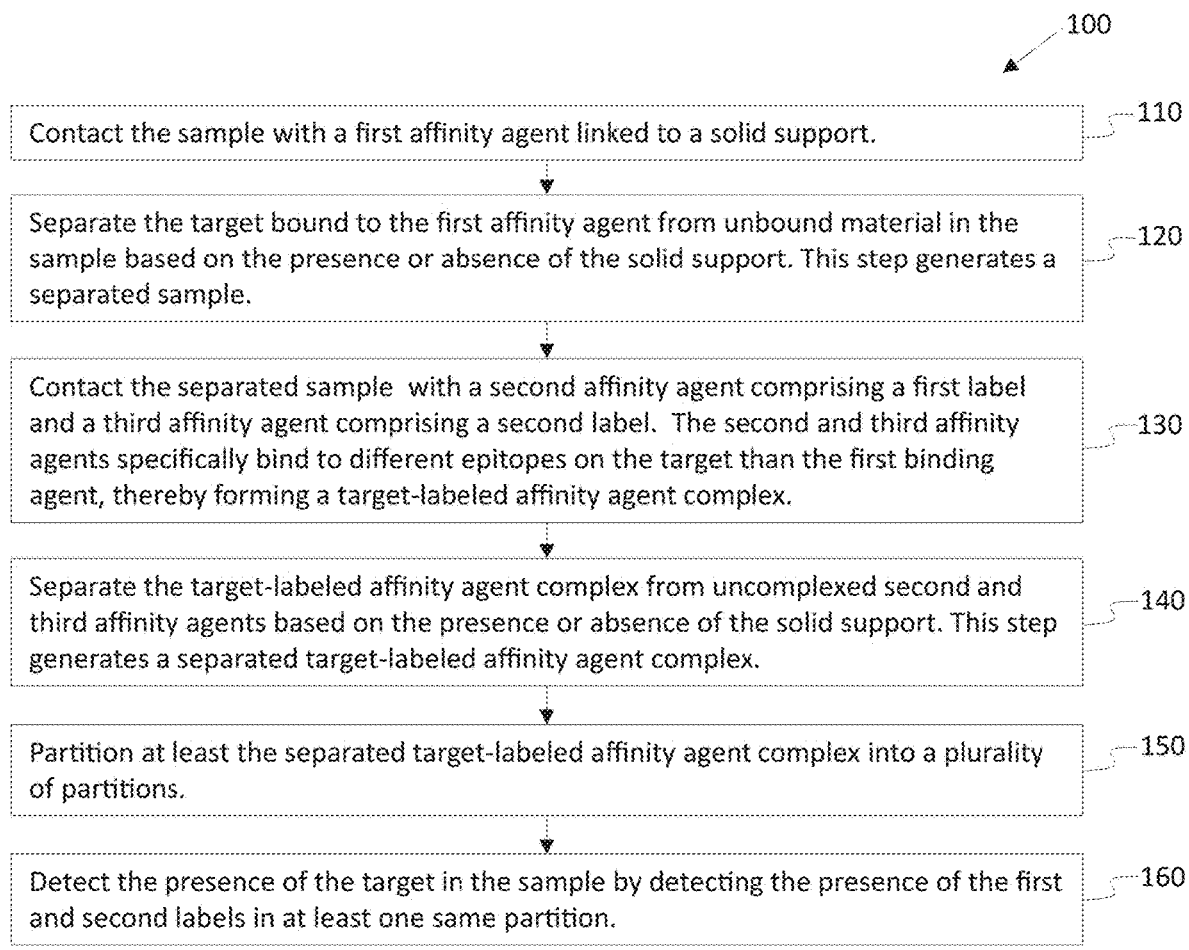
FIG. 1 is a flow chart showing a method of detecting a target in a sample according to an embodiment of the invention.
Figure 2:
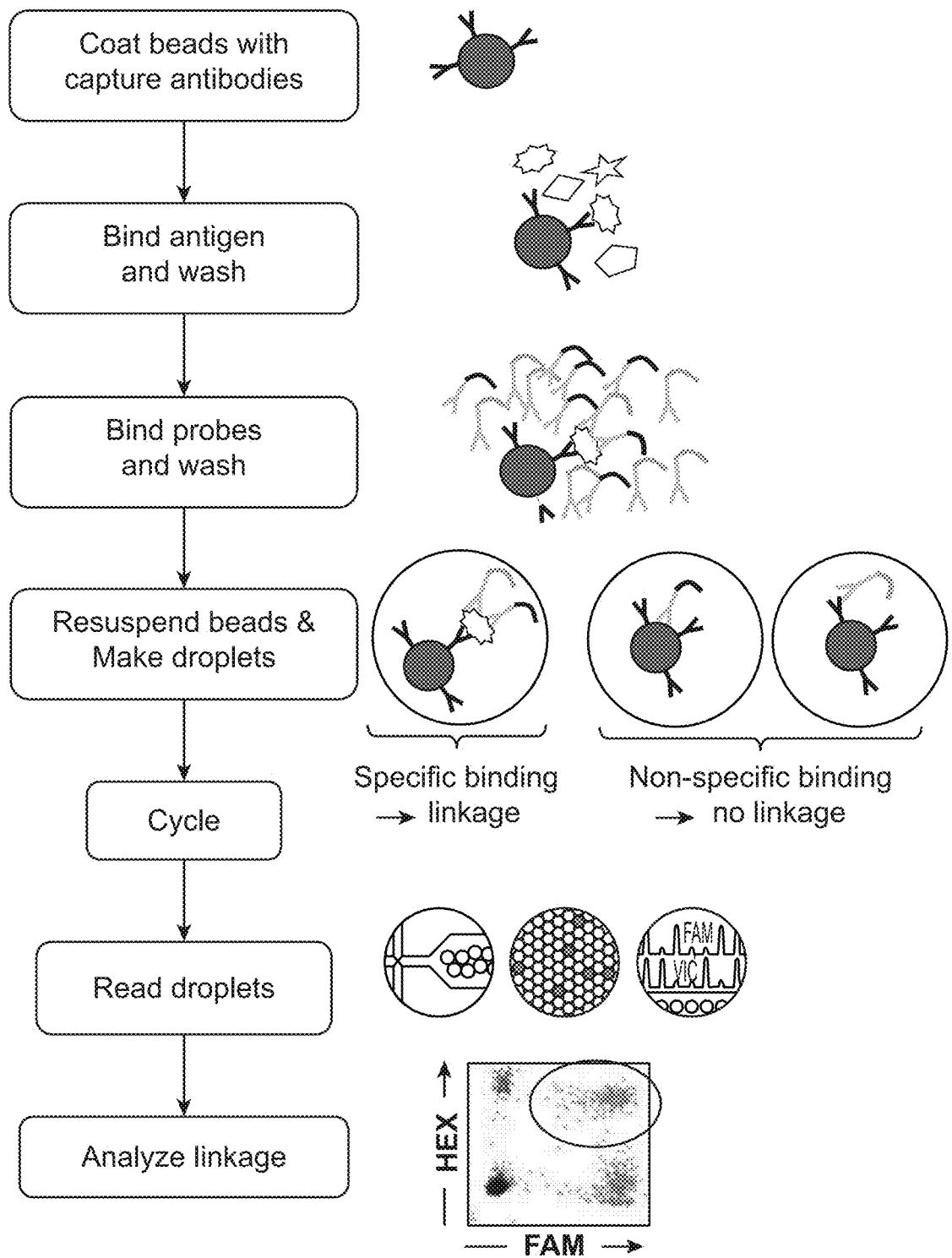
FIG. 2 describes the workflow of Example 1. Capture beads coated with the first affinity agent were reacted with the sample comprising the target antigen. A wash was performed to remove unbound components, then the target-bound beads were reacted with two different DNA-labeled affinity agents ("probes"). Some of the probes bound to the target-bound beads and the unbound probes were washed away. The complexes comprising the bead, target antigen, and labeled probes were then resuspended in a solution comprising an amplification mix and partitioned into droplets. ddPCR was performed and droplet fluorescence was measured. Linkage was determined according to the number of double positive droplets.

Described herein are methods of detecting a target in a sample. Digital affinity linkage assay methods have been discovered in which the concentration of a target is determined on a solid support by separating the sample into small partitions (e.g., droplets) and performing digital PCR analysis of two different DNA-labeled affinity agents (e.g. DNA-labeled antibodies). A linkage signal is calculated from the fraction of partitions in which the two different DNA labels are amplified and co-localized in the same partition.

As described herein, it has been surprisingly discovered that by using a solid support linked to an affinity agent in order to capture a target and wash away components other than the target-affinity agent complex, in combination with the use of two different labeled detection affinity agents and the subsequent linkage signal from co-localization of the two different labeled affinity agents for detection of a target, the background noise from non-specific binding of the affinity agents can be significantly reduced. Accordingly, the digital affinity linkage assay methods described herein have reduced background noise from non-specific binding of DNA-labeled affinity agents and have an unexpectedly high detection sensitivity or lower limit of detection. The methods described herein thus provide advantages such as the ability to detect significantly lower amounts of target in a sample as compared to assays in which targets are individually detected, and reducing or eliminating the need for diluting the concentration of affinity agents in a reaction mixture, thus avoiding the problem of diluting the affinity agents below the detection concentration.

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Green et al., MOLECULAR CLONING, A LABORATORY MANUAL (FOURTH EDITION), Cold Spring Harbor Lab Press (Cold Spring Harbor, N.Y. 2012).

The term "a" or "an" is intended to mean "one or more." The term "comprise," and variations thereof such as "comprises" and "comprising," when preceding the recitation of a step or an element, are intended to mean that the addition of further steps or elements is optional and not excluded. Any methods, devices and materials similar or equivalent to those described herein can be used in the practice of this invention. The following definitions are provided to facilitate understanding of certain terms used frequently herein and are not meant to limit the scope of the present disclosure.

The term "target" refers to any agent whose presence and/or amount is to be determined. In some embodiments, the target can be a mixture of several targets. In some embodiments the presence or concentration profile of the different targets is to be determined.

The target can be any biological and/or chemical agent (e.g., a molecule, macromolecule, complex, or conjugate). In some embodiments the target is an organic or inorganic molecule. In some embodiments the target is a biological agent.

In one embodiment the target is a protein, a protein aggregate, a protein oligomer, a polypeptide or a peptide. In some embodiments, the protein aggregate comprises more than one protein (e.g., more than one target). In some embodiments, the protein has more than one identical or non-identical subunit which may or may not be covalently bound to each other. The targets can be hormones, antibodies, amino acids (e.g., glutamic acid, aspartic acid) or any derivatives and/or combination thereof. In some embodiments the target is a toxin or a drug. In some embodiments, the amount of the target in the sample is in micrograms. In some embodiments, the amount of the target in the sample is below 1 microgram. In some embodiments, amount of the target in the sample is in nanograms. In some embodiments the amount of target in the sample is between 100 ng to 1 ng. In some embodiments, the amount of target in the sample is between 1000 pg to 1 pg. In certain embodiments, the amount of target in the sample is between 1 pg to 1 fg. In certain embodiments, the amount of target in the sample is between 1 fg to 1 ag.

The term "affinity agent" refers to a molecule that specifically binds to a target. Exemplary affinity agents include, but are not limited to, an antibody, an antibody fragment, a non-antibody protein scaffold, an antibody mimetic, or an aptamer.

The term "antibody" refers to a polypeptide of the immunoglobulin family or a polypeptide comprising fragments of an immunoglobulin that is capable of noncovalently, reversibly, and in a specific manner binding to a corresponding target (or antigen). The term includes, but is not limited to, polyclonal or monoclonal antibodies of the isotype classes IgA, IgD, IgE, IgG, and IgM, derived from human or other mammalian cells, including natural or genetically modified forms such as humanized, human, single-chain, chimeric, synthetic, recombinant, hybrid, mutated, grafted, and in vitro generated antibodies. The term encompasses conjugates, including but not limited to fusion proteins containing an immunoglobulin moiety (e.g., chimeric or bispecific antibodies or single chain Fv's (scFv's)), and fragments, such as Fab, F(ab')2, Fv, scFv, Fd, dAb and other compositions.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. The variable region contains the antigen-binding region of the antibody (or its functional equivalent) and is most critical in specificity and affinity of binding. See Paul, *Fundamental Immunology* (2003).

Antibodies can exist as intact immunoglobulins or as any of a number of well-characterized fragments that include specific antigen-binding activity. Such fragments can be produced by digestion with various peptidases. Pepsin digests an antibody below the disulfide bonds in the hinge region to produce $F(ab')_2$, a dimer of Fab which itself is a light chain joined to $V_H$-$C_H$1 by a disulfide bond. The $F(ab')_2$ can be reduced under mild conditions to break the disulfide bond in the hinge region, thereby converting the $F(ab')_2$ dimer into an Fab' monomer. The Fab' monomer is essentially Fab with part of the hinge region. While various antibody fragments are defined in terms of the digestion of an intact antibody, one of skill will appreciate that such fragments can be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., scFv) or those identified using phage display libraries (see, e.g., McCafferty et al. (1990) Nature 348:552-554). Methods for the preparation of antibodies are known in the art; see, e.g., Kohler & Milstein (1975) Nature 256:495-497; Kozbor et al. (1983) Immunology Today 4:72; Cole et al., Monoclonal Antibodies and Cancer Therapy, pp. 77-96. Alan R. Liss, Inc. 1985).

As used herein, the term "$F_V$" refers to a monovalent or bi-valent variable region fragment, and can encompass only the variable regions (e.g., $V_L$ and/or $V_H$), as well as longer fragments, e.g., an Fab, Fab' or F(ab')2, which also includes $C_L$ and/or $C_H1$. Unless otherwise specified, the term "Fc" refers to a heavy chain monomer or dimer comprising $C_H1$ and $C_H2$ regions.

The term "binds," as used with respect to an affinity agent binding to an antigen, typically indicates that the affinity agent (e.g., an antibody) binds a majority of the antigen in a pure population, assuming an appropriate molar ratio of affinity agent to antigen. For example, an affinity agent that binds a given antigen typically binds to at least ⅔ of the antigen molecules in a solution (e.g., 75%, 80%, 85%, 90%, 91%, 92%, 93%, 94%, 95%, 96%, 97%, 98%, 99%, or 100%). One of skill will recognize that some variability will arise depending on the method and/or threshold of determining binding.

The term "specifically binds to," as used with reference to an affinity agent, refers to an affinity agent (e.g., an antibody) that binds to an antigen with at least 2-fold greater affinity than to non-antigen molecules, e.g., at least 4-fold, 5-fold, 6-fold, 7-fold, 8-fold, 9-fold, 10-fold, 20-fold, 25-fold, 50-fold, 100-fold, $10^3$-fold, $10^4$-fold, $10^5$-fold. $10^6$-fold, $10^7$-fold, $10^8$-fold, $10^9$-fold, $10^{10}$-fold, $10^{11}$-fold, $10^{12}$-fold, $10^{13}$-fold, $10^{14}$-fold, or $10^{15}$-fold greater affinity. For example, an affinity agent that specifically binds a particular antigen will typically bind the antigen with at least a 2-fold greater affinity than to a non-antigen molecule.

As used herein, "nucleic acid" means a compound comprising a chain of nucleotide monomers. A nucleic acid can be single-stranded or double-stranded (i.e., base-paired with another nucleic acid), among others. The chain of a nucleic acid can be composed of any suitable number of monomers, such as at least about ten or one hundred, among others. Generally, the length of a nucleic acid chain corresponds to its source, with synthetic nucleic acids (e.g., nucleic acid reagents such as primers and probes) typically being shorter and biologically produced nucleic acids (e.g., nucleic acid analytes) typically being longer.

A nucleic acid can have a natural or artificial structure, or a combination thereof. Nucleic acids with a natural structure, namely, deoxyribonucleic acid (DNA) and ribonucleic acid (RNA), have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and can, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like. Similarly, nucleic acids having an artificial structure are analogs of natural nucleic acids and can, for example, be created by changes to the nucleobase. Exemplary artificial or non-naturally occurring nucleobases include, but are not limited to halogenated nucleobases (5-FU), hypoxanthine, xanthine, 7-methylguanine, inosine, xanthosine, 7-methyguanosine, 5,6-dihydrouracil, 5-methycytosine, 5-hydroxymethylcytosine, dihydrouridine, and 5-methylcytidine.

The sequence of a nucleic acid is defined by the order in which nucleobases are arranged along the backbone (typically read from the 5' to 3' end). This sequence generally determines the ability of the nucleic acid to bind specifically to a partner chain (or to form an intramolecular duplex) by hydrogen bonding. In particular, adenine pairs with thymine uracil) and guanine pairs with cytosine. A nucleic acid that can bind to another nucleic acid in an antiparallel fashion by forming a consecutive string of adenine-thymine and guanine-cytosine base pairs with the other nucleic acid is termed "complementary."

The terms "label", "detectable label", or "labeling agent" refer to a composition detectable by spectroscopic, photochemical, biochemical, immunochemical, chemical, or other physical means. For example, useful labels include fluorescent dyes (fluorophores), fluorescent quenchers, luminescent agents, electron-dense reagents, enzymes (e.g., as commonly used in an ELISA), biotin, digoxigenin, $^{32}P$ and other isotopes, haptens, proteins, nucleic acids, or other substances which can be made detectable, e.g, by incorporating a label into an oligonucleotide, peptide, or antibody specifically reactive with a target molecule. The term includes combinations of single labeling agents, e.g., a combination of fluorophores that provides a unique detectable signature, e.g., at a particular wavelength or combination of wavelengths. A detectable label can also include a combination of a reporter and a quencher.

A molecule that is "linked" to a label (e.g., as for a labeled nucleic acid as described herein) is one that is bound, either covalently, through a linker or a chemical bond, or noncovalently, through ionic, van der Waals, electrostatic, or hydrogen bonds to a label such that the presence of the molecule can be detected by detecting the presence of the label bound to the molecule.

The term "reporter" refers to a substance or a portion thereof which is capable of exhibiting a detectable signal, which signal can be suppressed by a quencher. The detectable signal of the reporter is, e.g., fluorescence in the detectable range; thus, a reporter can also be a label.

The term "quencher" refers to a substance which is capable of suppressing, reducing, inhibiting, etc., the detectable signal produced by the reporter.

As used herein, the term "quenching" refers to a process whereby, when a reporter and a quencher are in close proximity, and the reporter is excited by an energy source, a substantial portion of the energy of the excited state non-radiatively transfers to the quencher where it either dissipates nonradiatively or is emitted at a different emission wavelength than that of the reporter (e.g., by fluorescence resonance energy transfer or FRET).

The reporter can be selected from fluorescent organic dyes modified with a suitable linking group for attachment to the oligonucleotide, such as to the 3' or 5 terminus. The quencher can also be selected from organic dyes, which may or may not be fluorescent, depending on the embodiment of the invention. Generally, whether the quencher is fluorescent or simply releases the transferred energy from the reporter by non-radiative decay, the absorption band of the quencher should at least substantially overlap the fluorescent emission band of the reporter to optimize the quenching.

Non-fluorescent quenchers or dark quenchers typically function by absorbing energy from excited reporters, but do not release the energy radiatively.

Selection of appropriate reporter-quencher pairs for particular probes can be undertaken in accordance with known techniques. Fluorescent and dark quenchers and their relevant optical properties from which exemplary reporter-quencher pairs can be selected are listed and described, for example, in R. W. Sabnis, HANDBOOK OF FLUORESCENT DYES AND PROBES, John Wiley and Sons, New Jersey, 2015, the content of which is incorporated herein by reference.

Reporter-quencher pairs can be selected from xanthene dyes including fluoresceins and rhodantine dyes. Many suitable forms of these compounds are available commercially with substituents on the phenyl groups, which can be used as the site for bonding or as the bonding functionality for attachment to an oligonucleotide. Another group of fluorescent compounds for use as reporters are the naphthylamines, having an amino group in the alpha or beta position. Included among such naphthylamino compounds are 1-dimethylaminonaphthy 1-5 sulfonate, 1-anilino-8-naphthalene sulfonate and 2-p-touidiny 1-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like.

Suitable examples of quenchers can be selected from 6-carboxy-tetramethyl-rhodamine, 4-(4-dimethylaminophenylazo) benzoic acid (DABYL), tetramethylrhodamine (TAMRA), BHQ-OTM, BHQ-1 TM, BHQ-2TM, and BHQ-3TM, each of which are available from Biosearch Technologies, Inc. of Novato, Calif., Qy7TM QSY-9TM, QSY-21 TM and QSY-35TM, each of which are available from Molecular Probes, Inc, and ZEN™ and TAO™ Double-Quenched Probes from Integrated DNA Technologies.

Suitable examples of reporters can be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOETM available from Applied Biosystems), VICTM dye products available from Molecular Probes, Inc., NEDTM dye products available from Applied Biosystems, Cal Fluor dye products (such as, e.g., Cal Fluor Gold 540, Orange 560, Red 590, Red 610, Red 635) available from Biosearch Technologies, Quasar dye products (such as, e.g., Quasar 570, 670, 705) available from Biosearch Technologies, and the like.

The term "partitioning" or "partitioned" refers to separating an aqueous solution having one or more of a sample and reactant into a plurality of portions, or "partitions." Partitions can be solid or fluid. In some embodiments, a partition is a solid partition, e.g., a microchannel, a microtube, or a microwell. In some embodiments, a partition is a fluid partition, e.g., a droplet. In some embodiments, a fluid partition (e.g, a droplet) is a mixture of immiscible fluids (e.g., water and oil). In some embodiments, a fluid partition (e.g., a droplet) is an aqueous droplet that is surrounded by an immiscible carrier fluid oil).

III. Detection Methods

A method 100 of detecting a target in a sample will now be described. Some of the steps can be performed in any suitable order, in any suitable combination, and can be combined with or modified by any other suitable aspects of the disclosure provided herein.

In exemplary step 110, the sample is contacted with a first affinity agent (e.g., an antibody or antibody fragment) linked to a solid support. The first affinity agent specifically binds to a first epitope on the target, if present, thereby forming a target bound to the first affinity agent. In some embodiments, the sample is incubated with the first affinity agent to allow time for the first affinity agent to capture or bind to the target. In some embodiments, the sample is incubated with the first affinity agent for one hour or more. In some embodiments, prior to contacting the sample with the first affinity agent linked to the solid support, the solid support is treated with a blocking agent to prevent non-specific, binding of material to the support. Exemplary blocking agents include, but are not limited to, proteins (e.g., non-fat milk or bovine serum albumin) and detergents (e.g., Tween 20 or Triton X-100).

In some embodiments, the sample is a biological sample. Biological samples can be obtained from any biological organism, e.g., an annual, plant, fungus, bacterial, or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, transformed cells, stem cells, bacterial cells, stool, or urine.

In some embodiments, the sample can be prepared to improve the efficient detection of the target(s). For example, in some embodiments the sample can be fragmented, fractionated, homogenized, or sonicated. In some embodiments, a target of interest, or a sub-fraction comprising the target of interest, can be extracted or isolated from a sample (e.g., a biological sample). In some embodiments, the sample is enriched for the presence of the one or more targets. In some embodiments, the target is enriched in the sample by an affinity method, e.g., immunoaffinity enrichment. In some embodiments, the target is enriched in the sample using size selection (e.g., removing very small fragments or molecules or very long fragments or molecules).

Exemplary solid supports include, but are not limited to, particles (e.g., magnetic beads, polymeric beads, or silica-based beads) or a solid surface the surface of a reaction vessel such as a tube or a well in a plate). In some embodiments, the solid support is not chemically modified prior to the attachment of the first affinity agent antibody (e.g., the antibody is attached to the substrate by non-covalent adsorption, based on hydrophobic and other interactions). In certain embodiments, the solid support is chemically modified prior to the attachment of the first affinity agent. Exemplary chemically modified solid supports can have carboxyl or amine groups attached and these groups can be used to covalently bind the first affinity agent. In some embodiments, the first affinity agent is attached to the solid support via carbodiimide mediated chemistry to form an amide bond. In some embodiments, the attachment of the first affinity agent to the solid support is enhanced by a chemical or a photochemical reaction. In some embodiments, the first affinity agent is biotinylated and is attached to the solid support via an avidin-biotin or streptavidin-biotin interaction. In certain embodiments, the first affinity agent is permanently attached to the solid support by a chemical or a photochemical reaction. In some embodiments, the solid support is deactivated after attaching the first affinity agent to the solid support to prevent binding of other agents. For example, active carboxyl groups on the solid support can be deactivated with ethanolamine.

In exemplary step 120, the target bound to the first affinity agent is separated (e.g., the solid support is washed with a wash solution) from unbound material in the sample based on the presence or absence of the solid support, thereby generating a separated sample comprising the target bound to the first affinity agent. In some embodiments, a buffer comprising a detergent such as Tween 20 or Triton X-100 is used to remove or separate unbound material from the solid support. In some embodiments in which the solid support is a magnetic bead, the target bound to the first affinity agent is separated from the uncomplexed components in the sample using a magnet that attracts the magnetic beads linked to the first affinity agent. In some embodiments in which the solid support is a non-magnetic bead (e.g., polystyrene or silica-based beads), the target bound to the first affinity agent is separated from the uncomplexed components in the sample by centrifugation. In some embodiments in which the solid support is a surface of a reaction vessel (e.g., a tube or a well), the target bound to the first affinity agent is separated from the uncomplexed components in the sample by aspiration.

In exemplary step 130, the separated sample is contacted with a second affinity agent comprising a first label and a third affinity agent comprising a second label, wherein the second and third affinity agents specifically bind to the target, thereby forming a target-labeled affinity agent complex. In some embodiments, the second and third affinity agents specifically bind to different epitopes on the target than the first affinity agent. In some embodiments, the target (e.g., a dimeric protein, an aggregate-forming protein, or an oligomeric protein) has a repeating identical epitope such that the first and second affinity agents or the first and third affinity agents recognize the same epitope. In some embodiments, the target is a complex of two or more interacting proteins and the second and third affinity agents each bind to one of the interacting proteins in the complex. In certain embodiments, the target is a complex of two or more interacting partners (e.g., two proteins, a protein and a non-protein molecule(s), or non-protein molecules) and the method further comprises calculating a binding affinity (KD) of the interacting partners.

In certain embodiments (e.g., a multiplexing embodiment), the sample comprises a plurality of different targets, and for each of the plurality of different targets in the sample, a set of first, second, and third affinity agents is provided wherein each of the first, second, and third affinity agents specifically binds to the target. Thus, the first affinity agent is a plurality of different first affinity agents (i.e., each of the different first affinity agents binding to a different target in the sample), the second affinity agent is a plurality of different second affinity agents comprising a plurality of first labels (i.e., each of the different second affinity agents binding to a different target in the sample), and the third affinity agent is a plurality of different third affinity agents comprising a plurality of second labels (i.e., each of the different third affinity agents binding to a different target in the sample). A set of the first, second and third affinity agents specifically bind to the same one of the plurality of different targets.

In some embodiments, the first, second, and third affinity agents are antibodies, antibody fragments, or nucleotide aptamers. In certain embodiments, the antibodies are monoclonal antibodies or polyclonal antibodies.

In exemplary step 140, the target-labeled affinity agent complex is separated (e.g., the solid support is again washed) from uncomplexed second and third affinity agents based on the presence or absence of the solid support, thereby generating a separated target-labeled affinity agent complex.

In some embodiments, the first affinity agent is cleaved from the solid support prior to the next (partitioning) step, thereby releasing the target-labeled affinity agent complex from the solid support. In some embodiments, an amino acid tag linking the target-labeled affinity agent complex to the solid support is cleaved by a sequence-specific protease (e.g., TEV, factor Xa, or thrombin). In certain embodiments, a photo-cleavable linker between the solid surface and the first affinity agent is cleaved by exposing the linker to light. In some embodiments, the target-labeled affinity agent complex is cross-linked prior to partitioning the separated target-labeled affinity agent complex into a plurality of partitions.

In exemplary step 150, a plurality of partitions are formed from the separated target-labeled affinity agent complex such that a subset of the partitions contains the target-labeled affinity agent complex. The partitions can include any of a number of types of partitions, including solid partitions (e.g., wells or tubes) and fluid partitions (e.g., aqueous phase or droplet within an oil phase). In some embodiments, the partitions are droplets. In some embodiments, the partitions are microchannels or microwells. Methods and compositions for partitioning a solution are described, for example, in published patent applications WO 2012/135259, WO 2014/117088, WO 2010/036352, and U.S. Pat. No. 9,156,010, the entire content of each of which is incorporated by reference herein.

In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated coalesce with other droplets.

In an embodiment, the droplet is formed by flowing an oil phase through an aqueous phase. The oil for the oil phase can be synthetic or naturally occurring. In some embodiments, the oil comprises carbon and/or silicon. In some embodiments, the oil comprises hydrocarbon and/or fluorocarbon. Exemplary oils include, but are not limited to, silicone oil, mineral oil, fluorocarbon oil, vegetable oil, or a combination thereof.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0% 2.25%, 2.5%, 2.75%, or 3.0% (w/w). In some embodiments, 1H,1H, 2H,2H-Perfluorodecanol is added to a concentration of about 0.18% (w/w).

In some embodiments, the droplet is formed by flowing an oil phase through an aqueous solution phase having a DNA template and one or more components (e.g., reagents) that are used to determine the presence or absence of the target. In some embodiments, the one or more components used to determine the presence or absence of the target in the aqueous droplet are soluble and/or miscible in water including, but not limited to, one or more salts, buffering agents, reagents (e.g., a releasing agent such as a restriction endonuclease or a protease, PCR components), surfactants, and/or whatever additional components are necessary for a desired reaction(s) that is intended to occur within a formed droplet. All such additional components can be selected to be compatible with the desired reaction or intended assay.

In some embodiments, assay components (e.g., a DNA polymerase, dNTPs, and/or a PCR master mix, enzyme substrates) can be injected into the partition. The assay components can be injected into the partition in any order or simultaneously.

Methods of injecting fluids into partitions are described in, for example, WO 2012/135259 and US 2012/0132288, each of which is incorporated by reference in its entirety.

In some embodiments, at least 500 partitions (e.g., droplets), at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions are formed.

In some embodiments, the droplets that are generated are substantially uniform in shape and/or size. For example, in some embodiments, the droplets are substantially uniform in average diameter. The term "substantially" or "about" refers to the recited number and any value within 10% of the recited number. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, the partitions (e.g., droplets) are stable and are capable of long-term storage. In some embodiments, the partitions are stored at about −70°, −20°, 0°, 3°, 4°, 5°, 6°, 7°, 8°, 9°, 10°, 15°, 20°, 25°, 30°, 35°, or 40° C. for an extended period of time (e.g., for at least 30 days, at least 60 days, at least 90 days, or longer).

Partitions as described herein can contain one or more surfactants to reduce coalescence of droplets during transport. As used herein, a "surfactant" is a surface-active substance capable of reducing the surface tension of a liquid in which it is present. A surfactant, which also or alternatively is described as a detergent and/or a wetting agent, can incorporate both a hydrophilic portion and a hydrophobic portion, which can collectively confer a dual hydrophilic-hydrophobic character on the surfactant. A surfactant can, in some cases, be characterized according to its hydrophilicity relative to its hydrophobicity. In some embodiments, the aqueous phase incorporates at least one hydrophilic surfactant. The aqueous phase can include at least one nonionic surfactant and/or ionic surfactant. In certain embodiments, the aqueous phase includes a surfactant that is a block copolymer of polypropylene oxide and polyethylene oxide. In some embodiments, the surfactant is a block copolymer of polypropylene oxide and polyethylene oxide sold under the trade names PLURONIC and TETRONIC (BASF). In some embodiments, the surfactant is a nonionic block copolymer of polypropylene oxide and polyethylene oxide sold under the trade name PLURONIC F-68. In some embodiments, the surfactant of the aqueous phase is a water-soluble and/or hydrophilic fluorosurfactant. Exemplary fluorosurfactants for the aqueous phase are sold under the trade name ZONYL (DuPont), such as ZONYL FSN fluorosurfactants. In some cases, the surfactant can include polysorbate 20 (sold under the trade name TWEEN-20 by ICI Americas, Inc.). The concentration of a particular surfactant or total surfactant present in the aqueous phase can be selected to stabilize emulsion droplets prior to heating. In some embodiments, the concentration of surfactant for the aqueous phase is 0.01 to 10%, 0.05 to 5%, 0.1 to 1%, or 0.5% by weight.

In exemplary step 160, the presence of the target in the sample is detected by detecting the presence of the first and second labels in at least one same partition (i.e., the first and second labels are co-located in the same partition).

In certain embodiments, a method of detecting a target in a sample comprises contacting the sample with a first affinity agent linked to a solid support, a second affinity agent comprising a first label, and a third affinity agent comprising a second label. The first, second and third affinity agents specifically bind to the target, if present, thereby forming a target-labeled affinity agent complex. In some embodiments, the first, second, and third affinity agents specifically bind to different epitopes on the target. The next step comprises separating the target-labeled affinity agent complex from uncomplexed components in the sample based on the presence or absence of the solid support, thereby generating a separated target-labeled affinity agent complex. Next, the separated target-labeled affinity agent complex is partitioned into a plurality of partitions. The presence of the target is detected in the sample by detecting the presence of the first and second labels in at least one same partition.

In some embodiments, a method of detecting a target in a sample comprises contacting the sample with a second affinity agent comprising a first label and a third affinity agent comprising a second label. The second and third affinity agents specifically bind to the target, if present, thereby forming a first complex comprising the target, the second affinity agent, and third affinity agent. In some embodiments, the second and third affinity agents specifically bind to different epitopes on the target. The next step of the method comprises contacting the first complex with a first affinity agent linked to a solid support. The first affinity agent specifically binds to the target, thereby forming a target-labeled affinity agent complex comprising the target, the first affinity agent, the second affinity agent, and the third affinity agent. In some embodiments, the first affinity agent specifically binds to a different epitope on the target than the second and third affinity agents. Next, the target-labeled affinity agent complex is separated from uncomplexed components based on the presence or absence of the solid support, thereby generating a separated target-labeled affinity agent complex. At least the separated target-labeled affinity agent complex is then partitioned into a plurality of partitions. The presence of the target in the sample is detected by detecting the presence of the first and second labels in at least one same partition.

In certain embodiments, a method of detecting a target in a sample comprises conjugating a plurality of solid supports to a plurality of proteins in the sample comprising the target, if present, thereby forming a plurality of solid support conjugates. In some embodiments, the conjugating step comprises cross-linking. Cross-linking methods and reagents are known in the art, and include but are not limited to the use of carbodiimides, pryidyl disulfides, carbonyls, hydrazides, maleimides, haloacetyls, and diazirines. The next step comprises separating the plurality of solid support conjugates from unconjugated material in the sample based on the presence or absence of the plurality of solid supports, thereby generating a separated plurality of solid support conjugates. Next, the separated plurality of solid support conjugates are contacted with a first affinity agent comprising a first label and a second affinity agent comprising a second label. The first and second affinity agents specifically bind to different epitopes on the target, thereby forming a target-labeled affinity agent complex. In the next step, the target-labeled affinity agent complex is separated from uncomplexed first and second affinity agents based on the presence or absence of the solid support, thereby generating a separated target-labeled affinity agent complex. Next, at least the separated target-labeled affinity agent complex is partitioned into a plurality of partitions. The presence of the target in the sample is then detected by detecting the presence of the first and second labels in at least one same partition.

In some embodiments, the first and second labels are nucleic acid (e.g., DNA) labels. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length. In embodiments in which the nucleic acid label is an oligonucleotide, the oligonucleotide can be synthesized by methods known to those skilled in the art and are commercially available. First and second oligonucleotides used as first and second labels in embodiments herein are generally designed such that the first oligonucleotide does not hybridize with the second oligonucleotide. As used herein, "hybridize" refers to the process of forming a double stranded nucleic acid from joining two complementary strands of DNA or RNA.

In certain embodiments, the nucleic acid labels are amplified. The nucleic acid label can be amplified by, for example PCR, LCR (Ligase Chain Reaction), SDA (Strand Displacement Amplification), 3SR (Self-Sustained Synthetic Reaction), TMA (Transcription-Mediated Amplification), rolling circle amplification (RCA), or hyper-branched RCA (HRCA).

In some embodiments, the amplified nucleic acid labels are detected by direct incorporation of a label (e.g., a fluorophore, a radioisotope, or an enzyme) into the amplified nucleic acid by using label-conjugated primers or nucleotides. In some embodiments, a dye that fluoresces when it intercalates into double-stranded DNA is used to detect the amplified nucleic acids. Exemplary intercalating dyes include, but are not limited to, ethidium bromide, propidium iodide, EvaGreen® dye, and SYBR™ green. In some embodiments, the amplified nucleic acids are detected by using a nucleic acid probe having a reporter on one end and a quencher on the other end. In some embodiments, the probe comprises a reporter-quencher combination as employed in a TAQMAN™ probe, a molecular beacon probe, a SCORPION™ probe, a dual hybridization probe, a double-stranded probe, an ECLIPSE™ probe, or a double-quenched probe (e.g., ZEN™ or TAO™ Double-Quenched Probes from IDT). In some embodiments, the first and second nucleic acid labels are detected using different signal levels of the same DNA probe or intercalating dye. In embodiments using DNA probes, for each oligo label, the DNA probe is added at a different concentration. In embodiments using intercalating dyes, different signal intensity for each oligo label is created by either different amplicon length, or different concentration of primers. Droplets positive for a first label will have a mild increase in fluorescence, droplets positive for a second label will have an intermediate increase in fluorescence, and double positive droplets, which indicate linkage, will have the highest fluorescence signal.

In some embodiments, the first and second labels are different enzymes, and the target is detected by detecting a product generated by each of the enzymes. Examples of suitable enzymes include, but are not limited to, urease, alkaline phosphatase, (horseradish) hydrogen peroxidase (HRP), glucose oxidase, β-galactosidase, luciferase, and an esterase. For example, a horseradish-peroxidase detection system can be used with the fluorogenic substrate 10-acetyl-3,7-dihydroxyphenoxazine (ADHP), which in the presence of hydrogen peroxide yields Resorufin, a soluble product that is detectable at 585 nm. An alkaline phosphatase detection system can be used with the fluorogenic substrate Fluorescein Diphosphate (FDP), which yields a soluble product readily detectable at 520 nm. A β-galactosidase detection system can be used with the fluorogenic substrate Resorufin β-D-Galactopyranoside (RBG), which yields a soluble product detectable at 585 nm. An esterase detection system can be used with a substrate such as fluorescein diacetate. In some embodiments, 2, 3, 4, 5, or more affinity agents used for detecting a target molecule are each labeled with an enzyme (e.g., a first affinity agent labeled with a first enzyme, a second affinity agent labeled with a second enzyme, etc.), and each affinity agent that is labeled with an enzyme is detected by detecting a distinguishable product generated by the enzyme.

In some embodiments, labels are linked to affinity agents by biotin-streptavidin interaction. In some embodiments, the first and second labels are each linked to streptavidin and the second and third affinity agents are biotinylated. The second and third affinity agents are labeled prior to a first step of any of the methods described herein by allowing the first and second labeled streptavidins to bind to the respective biotinylated second and third affinity agents.

The detectable label (e.g., a label as described herein) can be detected using any of a variety of detector devices. Exemplary detection methods include optical absorbance detection (e.g., fluorescence or chemiluminescence) or radioactive detection. As a non-limiting example, a fluorescent label can be detected using a detector device equipped with a module to generate excitation light that can be absorbed by a fluorophore, as well as a module to detect light emitted by the fluorophore.

In some embodiments, the detector further comprises handling capabilities for the partitioned samples (e.g., droplets), with individual partitioned samples entering the detector, undergoing detection, and then exiting the detector. In some embodiments, partitioned samples (e.g., droplets) are detected serially while the partitioned samples are flowing. In some embodiments, partitioned samples (e.g., droplets) are arrayed on a surface and a detector moves relative to the surface, detecting signal(s) at each position containing a single partition. Examples of detectors are provided in WO 2010/036352, the contents of which are incorporated herein by reference. In some embodiments, detectable labels in partitioned samples are detected serially without flowing the partitioned samples (e.g., using a chamber slide).

Following acquisition of fluorescence detection data, a general purpose computer system (referred to herein as a "host computer") can be used to store and process the data. Computer-executable logic can be employed to perform such functions as subtraction of background signal, assignment of target and/or reference sequences, and qualification and/or quantification of the data. A host computer can be useful for displaying, storing, retrieving, or calculating diagnostic results from the molecular profiling; storing, retrieving, or calculating raw data from expression analysis; or displaying, storing, retrieving, or calculating any sample or patient information useful in the methods of the present invention.

The host computer can be configured with many different hardware components and can be made in many dimensions and styles (e.g., desktop PC, laptop, tablet PC, handheld computer, server, workstation, mainframe). Standard components, such as monitors, keyboards, disk drives, CD and/or DVD drives, and the like, can be included. Where the host computer is attached to a network, the connections can be provided via any suitable transport media (e.g., wired, optical, and/or wireless media) and any suitable communication protocol (e.g., TCP/IP); the host computer can include suitable networking hardware (e.g., modem, Ethernet card, WiFi card). The host computer can implement any of a variety of operating systems, including UNIX, Linux, Microsoft Windows, MacOS, or any other operating system.

Computer code for implementing aspects of the present invention can be written in a variety of languages, including PERL, C, C++, Java, JavaScript, VBScript, AWK, or any other scripting or programming language that can be executed on the host computer or that can be compiled to execute on the host computer. Code can also be written or distributed in low level languages such as assembler languages or machine languages.

The host computer system advantageously provides an interface via which the user controls operation of the tools. In the examples described herein, software tools are implemented as scripts (e.g., using PERL), execution of which can be initiated by a user from a standard command line interface of an operating system such as Linux or UNIX. Those skilled in the art will appreciate that commands can be adapted to the operating system as appropriate. In other embodiments, a graphical user interface can be provided, allowing the user to control operations using a pointing device. Thus, the present invention is not limited to any particular user interface.

Scripts or programs incorporating various features of the invention as described herein can be encoded on various computer readable media for storage and/or transmission. Examples of suitable media include magnetic disk or tape, optical storage media such as compact disk (CD) or DVD (digital versatile disk), flash memory, and carrier signals adapted for transmission via wired, optical, and/or wireless networks conforming to a variety of protocols, including the Internet.

In some embodiments, the methods further comprise quantifying the target (e.g., a protein, a protein aggregate, or a protein oligomer) by determining a number of partitions comprising both the first and second labels and determining a total number of partitions. Once a binary "yes-no" result has been determined for each of the partitions, the data for the partitions is analyzed by an algorithm based on Poisson statistics to quantify the amount of target in the sample. In some embodiments, the degree or amount of linkage between the two labels is proportional to the degree or amount of protein aggregation or protein oligomerization and is used to quantify the amount of aggregation or oligomerization. An exemplary statistical method for quantifying the concentration or amount of target or targets is described, for example in the aforementioned WO 2010036352.

IV. Kits

In another aspect, kits for detecting a target or a plurality of targets in a sample according to the methods described herein are provided. In some embodiments, a kit comprises a first affinity agent linked to a solid support, a second affinity agent conjugated to a first label, and a third affinity agent conjugated to a second label, wherein each of the first, second, and third affinity agents specifically binds to the target. In embodiments in which the target is a plurality of targets, for each of the plurality of different targets in the sample, a set of first, second, and third affinity agents is provided wherein each of the first, second, and third affinity agents specifically binds to the target. Affinity agents, affinity agents linked to a solid support, and affinity agents conjugated to labels are described herein.

In some embodiments, the first label is a first oligonucleotide and the second label is a second oligonucleotide. In this embodiment, the kit can further comprise assay components (e.g., a DNA polymerase, PCR primers, PCR probes, dNTPs, a buffer, a PCR master mix).

In certain embodiments, the first label is a first enzyme and the second label is a second enzyme. In this embodiment, the kit can further comprise enzyme substrates for each of the first and second enzymes.

In some embodiments, the kit comprises a chemically modified solid support, a first label, and a second label, wherein the first and second labels are each linked to streptavidin. Solid supports and labels are described herein. In some embodiments, the chemically modified solid support can be linked to a first affinity agent supplied by the user. In some embodiments, the first and second labeled streptavidins can bind to biotinylated second and third affinity agents, respectively, supplied by the user. In some embodiments, the kit comprises a streptavidin-coated solid support. The streptavidin-coated solid support can be linked to a biotinylated first affinity agent supplied by the user.

In some embodiments, the kit further comprises instructions for carrying out the methods described herein.

EXAMPLES

The following examples are provided by way of illustration only and not by way of limitation. Those of skill in the art will readily recognize a variety of non-critical parameters that could be changed or modified to yield essentially the same or similar results.

Example 1

Quantitation of Target With a Digital Affinity Linkage Assay Using Monoclonal Antibodies In this example, two individual immuno-PCR assays were compared to a digital affinity linkage assay according to the invention. Purified human Decorin was used as the target protein and three different monoclonal Decorin antibodies were used: one antibody for the capture and the other two antibodies for detection.

Capture beads were prepared by binding biotinylated monoclonal Decorin antibody (R&D systems) to Streptavidin coated 1 μm tysolactivated magnetic beads (Dynabeads™ MyOne™ Streptavidin T1, Thermo Fisher Scientific). The beads were first washed three times with Dulbecco's phosphate buffered saline pH 7.4 (PBS, Biological Industries, Israel). Next, the beads were mixed with biotinylated Decorin antibody at a ratio of 40 μg antibody/$2 \times 10^9$ beads in a volume of 280 μl in PBS buffer and incubated at room temperature for 2 hours. The beads were washed from residual antibody five times in PBS supplemented with 0.1% Bovine serum albumin (BSA, Merck).

The detection antibodies were prepared from two different clones of Decorin monoclonal antibodies (R&D systems) directly conjugated to amine modified 100 base long DNA oligonucleotides (IDT) by Innova Biosciences, UK. The conjugates were purified from unbound oligonucleotides.

For each sample, $3 \times 10^7$ capture beads were incubated with 200 μl PBS supplemented with 0.01% tween-20 (PBS-T, Merck) and 0.1% BSA for 15 minutes. The blocking solution was removed by aspiration after magnetizing the beads. The beads were resuspended in 25 μl of PBS-T supplemented with HeLa cell lysate (Ipracell, Belgium) at 25 μg/ml and spiked with concentration series of Human recombinant Decorin (R&D systems) at range of 100 ng/ml-10 fg/ml. The beads and samples were incubated for 1.5 hours at room temperature on a rotator. In order to measure background levels, four Non-Protein Controls (NPC) were prepared in which no Decorin was spiked into the HeLa cell lysate. Following the binding reaction, the beads were washed three times in 200 μl PBS-T.

The beads were then incubated in 50 μl of a mixture of both detection probes each at a concentration of 2 nM in PBS-T supplemented with 0.1% BSA and 100 ng/μl Polyadenylic acid (Merck). The probes were allowed to bind the beads for 1.5 hours at room temperature while rotating. After the incubation, unbound detection probes were washed five times in PBS-T and the beads were resuspended in 100 μl TE solution pH 8.0 (Merck). One μl of each sample was further diluted in 99 μl TE solution to reach bead concentration of 3,000 beads/μl.

Finally, the amplification mix containing PCR primers, TaqMan probes, dNTPs and DNA polymerase was prepared and mixed with the samples. Droplets were generated in QX200™ Droplet Generator (Bio-Rad).

Amplification mix contained (per sample): 12 μl ddPCR supermix for probes (Bio-Rad), 1.2 μl of 10 μM amplification primers (forward and reverse primer for each label), 0.5 μl of 10 μM FAM hydrolysis probe for the first label, 0.5 μl of 10 μM HEX hydrolysis probe for the second label (all oligonucleotides were purchased from IDT) and 6.5 μl diluted sample.

Droplets were generated from 20 μl amplification mix, placed in ddPCR plates (Bio-Rad), sealed with Microseal 'F' PCR plate seal (Bio-Rad) and placed in C1000 Thermal Cycler (Bio-Rad) for amplification. For each sample, four PCR reactions were prepared and approximately 80,000 beads analyzed.

PCR cycles: hold 10 minutes at 95° C., cycle 94° C. for 30 seconds and 56° C. for 1 minute 40 times, hold 98° C. for 10 minutes. Droplet fluorescence was measured by the QX200™ Droplet Reader instrument (Bio-Rad) and for each sample the number of positive and negative droplets for each label was documented. Label concentration was calculated by the QuantaSoft™ Software according to Poisson distribution. Assay results are calculated automatically by the software in the "Linkage" output by calculating the number of double positive droplets observed above the expected number from random distribution.

Fitting the data to 4 parameter logistics (4PL) model was performed using GraphPad Prism version 7.02, GraphPad Software, California USA.

Figure 3:
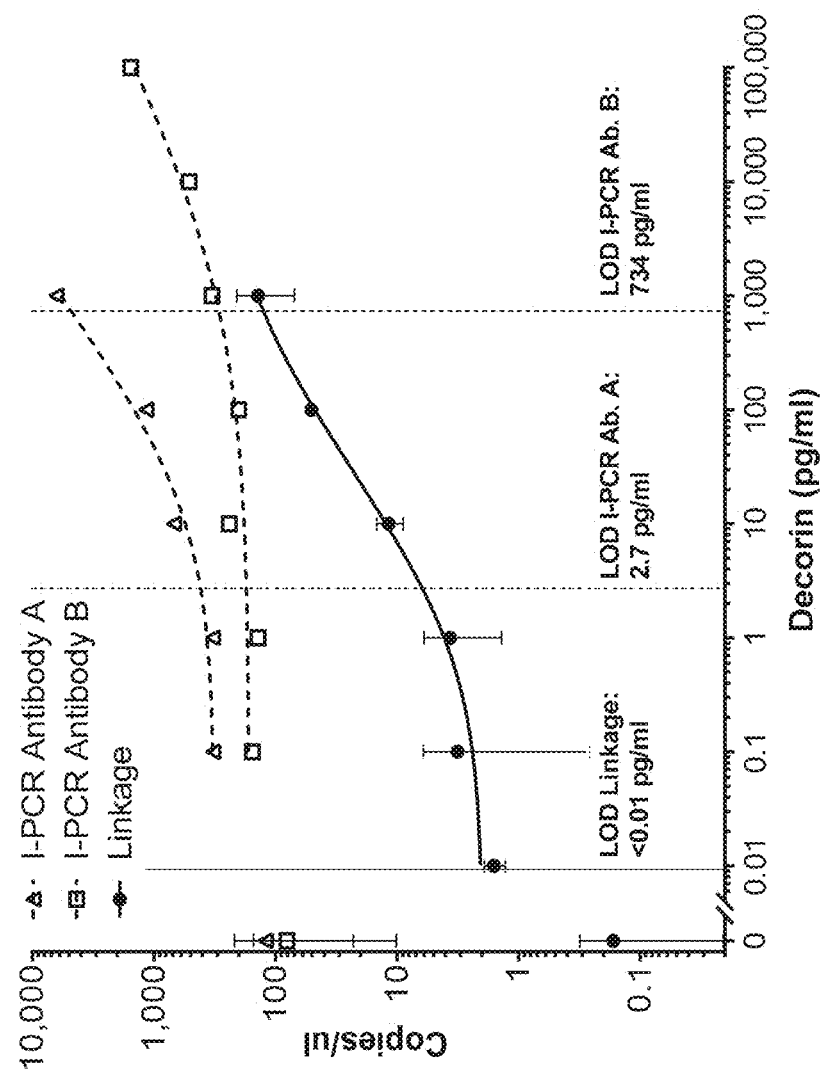
FIG. 3 shows dose response curves for an experiment as described in Example 1 (quantitation of a target protein using monoclonal antibodies). The results from two individual immuno-PCR assays (triangle and square markers with dashed curves) were compared to an affinity linkage assay with the same two DNA-labeled monoclonal antibodies (circle markers with solid curve). The vertical lines mark the calculated Limit of Detection (LOD) values.

Results of the two immuno-PCR assays and the digital affinity linkage assay are summarized in FIG. 3. The results show relatively high Limit of Detection (LOD) values for the individual labeled antibodies used in an immuno-PCR assay (triangle and square markers with dashed curve). However, when the same data is reused to calculate the linkage signal (circle markers with solid curve), the noise level is significantly reduced, enabling detection of much lower target concentrations and extending the dynamic range by three orders of magnitude. These results suggest an unexpected 10 to 100 fold improvement in the signal to noise ratio when comparing results from individual immuno-PCR assays to an affinity linkage assay.

Example 2

Quantitation of Target With a Digital Affinity Immuno-Assay Linkage Assay Using Polyclonal Antibodies In this example, two individual immuno-PCR assays were compared to a digital affinity linkage assay for three different protein targets according to the invention. Purified human antigens (PSA, EGF or IL-10) were used as the target proteins and for each target a single polyclonal antibody (targeting PSA. EGF or IL-10) was used both for the capture and for the detection.

Capture beads were prepared for each target by binding the relevant biotinylated poly clonal antibody (R&D systems) to Streptavidin coated 1 µm tysolactivated magnetic beads (Dynabeads™ MyOne™ Streptavidin T1, Thermo Fisher Scientific). 200 µl of the beads at stock concertation of $7$-$10 \times 10^9$ beads/mL were transferred to an Eppendorf tube and the buffer was removed by magnetizing the beads and aspirating the supernatant. The beads were resuspended in 200 µl Dulbecco's phosphate buffered saline pH 7.4 (PBS, Biological Industries, Israel) supplemented with 50 nM biotinylated polyclonal antibody (R&D systems). Next, the heads were incubated with rotation at room temperature for 1 hour. The beads were washed from residual antibody two times in PBS supplemented with 0.05% tween-20. Finally, the beads were resuspended in 200 µl PBS supplemented with 0.1% Bovine serum albumin (BSA, Merck) and stored at 4° C.

Streptavidin conjugated to oligonucleotide tags was prepared in advance in the following manner. Two 5' amino modified 70-80 bases long oligonucleotide were designed and ordered from IDT. The oligonucleotides were designed to have no significant homology to each other or to other natural sequences. They were separately covalently conjugated to Pierce™ Streptavidin (Thermo Fisher Scientific) with the Protein-Oligo Conjugation Kit (TriLink BioTechnologies) according to manufacturer's instructions. Protein concentration and nucleotide concentration in the resulting conjugate were determined by UV absorption.

Before each experiment, the detection antibodies labeled with one of the two oligonucleotide tags were prepared in two separate tubes. 2 µl of 1 µM biotinylated polyclonal antibodies were mixed with 2 µl of 1 µM (protein concentration) streptavidin-oligo conjugate and 36 µl PBS supplemented with 0.1% BSA (Merck). Antibodies and conjugate were incubated at room temperature for 1 hour and stored at 4° C.

For each sample, ~$1 \times 10^6$ capture beads were removed from storage buffer and resuspended in 5 µl blocking solution consisting of PBS pH 7.4 (Biological Industries, Israel), 1 mM D-Biotin (Thermo Fisher Scientific), 1 mg/mL BSA (Merck), 0.05% Tween-20 (Merck), 100 nM goat IgG (Merck), 0.1 mg/mL Salmon sperm single strand DNA (Thermo Fisher Scientific) and 5 nM Ethylenediaminetetraacetic acid disodium salt dihydrate (EDTA, Merck). 45 µl of blocking solution supplemented with HeLa cell lysate (Ipracell, Belgium) at 25 µg/ml, and spiked with concentration series of human recombinant PSA/EGF/IL-10 (R&D systems) at range of 100 ng/ml-10 fg/ml, were added to each sample of beads. The beads and samples were incubated for 1.5 hours at room temperature, shaking at 1200 rpm. In order to measure background levels, Non-Protein Controls (NPC) were prepared in which no antigen was spiked into the HeLa cell lysate. Following the binding reaction, the beads were washed twice in 150 µl PBS-T (PBS with 0.05% Tween-20) by magnetizing the beads, removing the supernatant and resuspending the beads in fresh solution.

The beads were then incubated in 50 µl of a mixture of both detection probes each at a concentration of 62.5 nM in blocking solution. The probes were allowed to bind the beads for 1.5 hours at room temperature while shaking. After the incubation, unbound detection probes were washed three times in PBS-T and the heads were resuspended in 120 µl TE solution pH 8.0 (Merck) to a final concentration of 8,333 beads/µl.

Finally, the amplification mix containing PCR primers, TaqMan probes, dNTPs and DNA polymerase was prepared and mixed with the samples. Droplets were generated in QX200™ Droplet Generator (Bio-Rad).

Amplification mix contained (per sample): 12 µl ddPCR supermix for probes (Bio-Rad), 1.2 µl of 10 µM amplification primers (forward and reverse primer for each label), 0.5 µl of 10 µM FAM hydrolysis probe for the first label, 0.5 µl of 10 µM HEX hydrolysis probe for the second label (all oligonucleotides were purchased from IDT), 4.2 µl double distilled water and 2 µl beads.

Droplets were generated from 20 µl amplification mix, placed in ddPCR plates (Bio-Rad), sealed with Microseal 'F' PCR plate seal (Bio-Rad) and placed in C1000 Thermal Cycler (Bio-Rad) for amplification. For each sample, two PCR reactions were prepared and approximately 33,000 beads analyzed.

PCR cycles: hold 10 minutes at 95° C., cycle 94° C. for 30 seconds and 56° C. for 1 minute 40 times, hold 98° C. for 10 minutes. Droplet fluorescence was measured by the QX200™ Droplet Reader instrument (Bio-Rad) and for each sample the number of positive and negative droplets for each label was documented. Label concentration was calculated by the QuantaSoft™ Software according to Poisson distribution. Assay results are calculated automatically by the software in the "Linkage" output by calculating the number of double positive droplets observed above the expected number from random distribution. Fitting the data to 4 parameter logistics (4PL) model was performed using GraphPad Prism version 7.02, GraphPad Software, California USA.

Figure 4B:
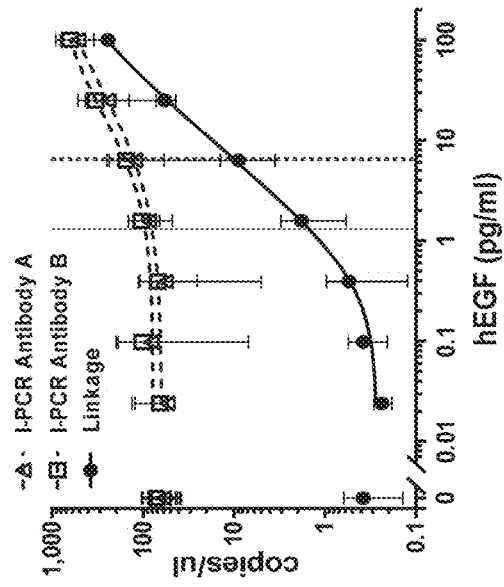
FIGS. 4A-4C show dose response curves for experiments as described in Example 2 (quantitation of different target proteins using polyclonal antibodies). For each target protein, the results from two individual immuno-PCR assays (triangle and square markers with dashed curves) were compared to an affinity linkage assay with the same two DNA-labeled polyclonal antibodies (circle markers with solid curve). The vertical lines mark the calculated LOD values for the individual Immuno-PCR assays vs. the digital affinity linkage assays.
Figure 4A:
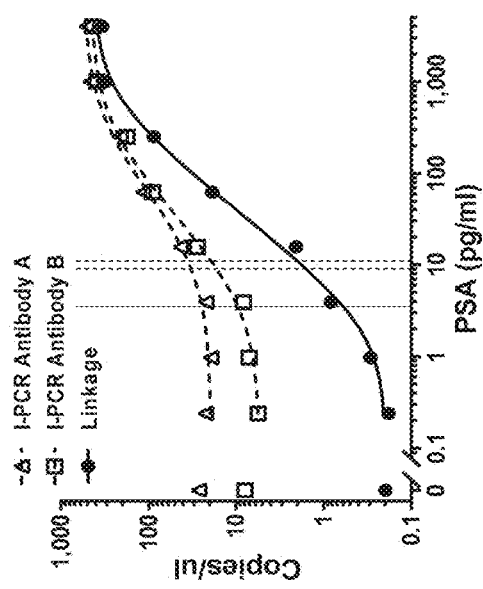
Figure 4C:
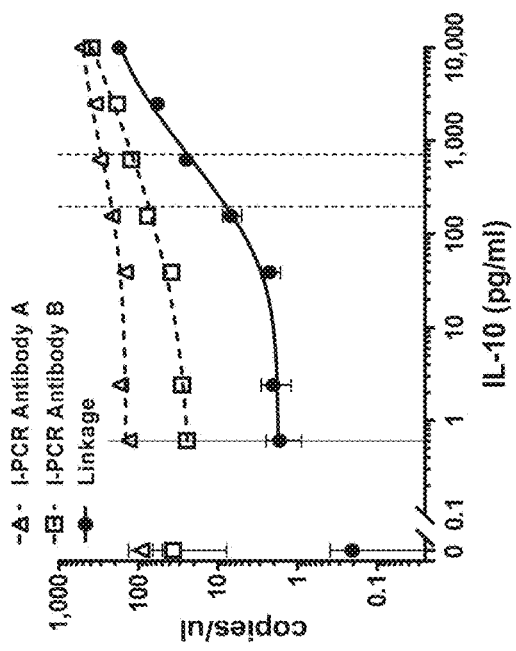

Results of the three sets of immuno-assays are summarized in FIGS. 4A-4C and Table 1.

TABLE 1

Limit of Detection values for individual Immuno-PCR assays vs. digital affinity linkage assays using the same two probes, prepared from polyclonal antibody

| Target Protein | LOD I-PCR Antibody A probe pg/mL | LOD I-PCR Antibody B probe pg/mL | LOD Digital Affinity Linkage Assay pg/mL |
|---|---|---|---|
| PSA | 11 | 9 | 3.5 |
| hEGF | 6.3 | 6.6 | 1.3 |
| IL-10 | 200 | 700 | <0.6 |

The results show improvement in the LOD values for each of the three targets when comparing the results of the individual immuno-PCRs (triangle and square markers and dashed lines) with the linkage results (circle markers and solid lines). The background noise levels calculated from the NPCs dropped 100-1000 fold between the immuno-PCR and linkage assay, resulting in improved LODs.

Example 3

Multiplex Quantitation of Several Targets With a Digital Affinity Immuno-Assay Linkage Assay Using Polyclonal Antibodies In this example, three immuno-assays for three different protein targets were performed in a single reaction according to the invention. Purified human antigens (PSA, EGF and IL-10) were used as the target proteins and three polyclonal antibodies (targeting PSA, EGF and IL-10) were used both for the capture and for the detection.

Capture beads were prepared separately for each target by binding the relevant biotinylated polyclonal antibody (R&D systems) to Streptavidin coated 1 µm tysolactivated magnetic beads (Dynabeads™ MyOne™ Streptavidin T1, Thermo Fisher Scientific). 200 µl of the beads at stock concertation of 7-10×10$^9$ beads/mL were transferred to an Eppendorf tube and the buffer was removed by magnetizing the beads and aspirating the supernatant. The beads were resuspended in 200 µl Dulbecco's phosphate buffered saline pH 7.4 (PBS, Biological Industries, Israel) supplemented with 50 nM biotinylated polyclonal antibody (R&D systems). Next, the beads were incubated with rotation at room temperature for 1 hour. The beads were washed from residual antibody two times in PBS supplemented with 0.05% tween-20. Finally, the beads were resuspended in 66.6 µl PBS supplemented with 0.1% Bovine serum albumin (BSA, Merck) and stored at 4° C.

Streptavidin conjugated to oligonucleotide tags was prepared in advance in the following manner. For each target analyzed, two 5' amino modified 70-80 bases long oligonucleotide were designed and ordered from IDT. The oligonucleotides were designed to have no significant homology to each other or to other natural sequences. They were separately covalently conjugated to Pierce™ Streptavidin (Thermo Fisher Scientific) with the Protein-Oligo Conjugation Kit (TriLink BioTechnologies) according to manufacturer's instructions. Protein concentration and nucleotide concentration in the resulting conjugate were determined by Pierce™ BCA protein assay (ThermoFisher Scientific) and UV absorption.

Before the experiment, the detection antibody for each target was labeled with two unique oligonucleotide tags in two separate tubes. 2 µl of 1 µM biotinylated polyclonal antibodies were mixed with 2 µl of 1 µM (protein concentration) streptavidin-oligo conjugate and 36 µl PBS supplemented with 0.1% BSA (Merck). Antibodies and conjugate were incubated at room temperature for 1 hour and stored at 4° C.

For each sample, 1-2×10' capture beads for each target (total of 3-6×10$^6$ beads) were removed from storage buffer and resuspended in 5 µl blocking solution which was composed of PBS pH 7.4 (Biological Industries, Israel). 1 mM D-Biotin (Thermo Fisher Scientific), 1 mg/mL BSA (Merck), 0.05% Tween-20 (Merck), 100 nM goat IgG (Merck), 0.1 mg/mL Salmon sperm single strand DNA (Thermo Fisher Scientific) and 5 mM Ethylenediaminetetraacetic acid disodium salt dihydrate (EDTA, Merck). 45 µl of blocking solution supplemented with HeLa cell lysate (Ipracell, Belgium) at 25 µg/ml, and spiked with a mixture of human recombinant PSA, EGF and IL-10 (R&D systems) concentration series at range of 100 ng/ml-10 fg/ml, was added to each sample of beads. The beads and samples were incubated for 1.5 hours at room temperature, shaking at 1200 rpm. In order to measure background levels, Non-Protein Controls (NPC) were prepared in which no antigens were spiked into the HeLa cell lysate. Following the binding reaction, the beads were washed twice in 150 µl PBS-T (PBS with 0.05% Tween-20) by magnetizing the beads, removing the supernatant and resuspending the beads in fresh solution.

The beads were then incubated in 50 µl of a mixture of six detection probes (two detection probes for each antigen), each probe at a concentration of 62.5 nM in blocking solution. The probes were allowed to bind the beads for 1.5 hours at room temperature while shaking. After the incubation, unbound detection probes were washed three times in PBS-T and the beads were resuspended in 120 µl TE solution pH 8.0 (Merck) to a final concentration of 25,000-50,000 beads/µl.

Amplification mixes containing PCR primers, TaqMan probes, dNTPs and DNA polymerase were prepared separately for the detection of each target. Each amplification mix contained (per target per sample): 12 µl ddPCR supermix for probes (Bio-Rad), 1.2 µl of 10 uM amplification primers (forward and reverse primer for each of the two labels), 0.5 µl of 10 µM FAM hydrolysis probe for the first label, 0.5 µl of 10 µM HEX hydrolysis probe for the second label (all oligonucleotides were purchased from IDT) and 4 µl double distilled water. 2 µl of the bead-bound immuno-complexes were then added to the three different amplification mixes and droplets were generated in QX200™ Droplet Generator (Bio-Rad).

Droplets were generated from 20 µl amplification mix, placed in ddPCR plates (Bio-Rad), sealed with Microseal 'F' PCR plate seal (Bio-Rad) and placed in C1000 Thermal Cycler (Bio-Rad) for amplification. For each sample and each target, two PCR reactions were prepared and approximately 33,000-66,000 beads analyzed.

PCR cycles: hold 10 minutes at 95° C. cycle 94° C. for 30 seconds and 56° C. for 1 minute 40 times, hold 98° C. for 10 minutes. Droplet fluorescence was measured by the QX200™ Droplet Reader instrument (Bio-Rad) and for each sample the number of positive and negative droplets for each label was documented. Label concentration was calculated by the QuantaSoft™ Software according to Poisson distribution. Assay results were calculated automatically by the software in the "linkage" output by calculating the number of double positive droplets observed above the expected number from random distribution, for each target separately. Fitting the data to 4 parameter logistics (4PL) model was performed using GraphPad Prism version 7.02, GraphPad Software, California USA.

Figure 5:
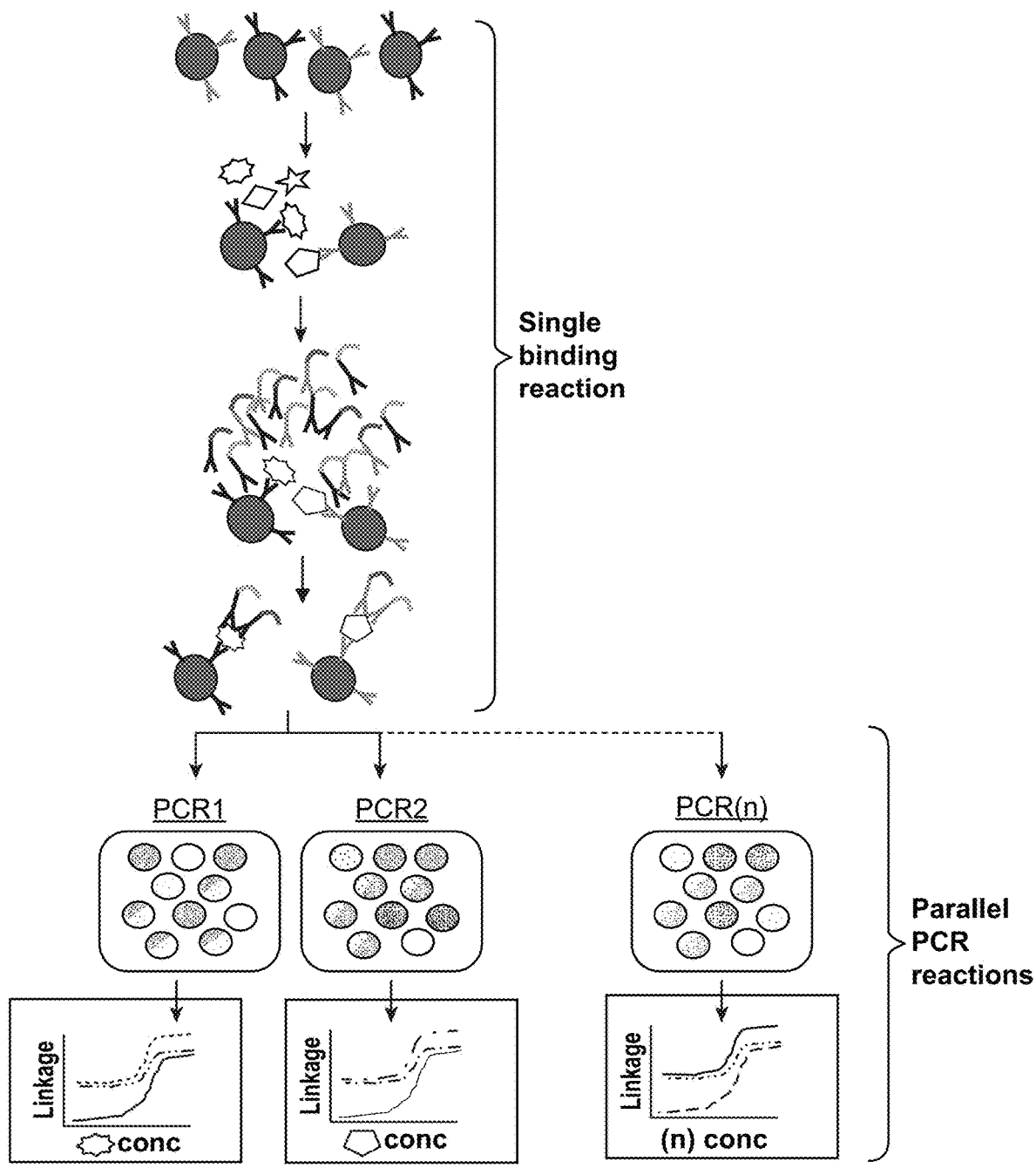
FIG. 5 illustrates a proposed workflow for multiplex protein quantitation of different targets with a digital affinity linkage assay.

FIG. 5 illustrates the workflow for multiplex protein quantitation of different targets with a digital affinity linkage assay.

Results of an experiment comparing a multiplex linkage affinity assay for three targets with three singleplex linkage affinity assays for the same targets are summarized in FIGS. 6A-6C and Table 2.

TABLE 2

Intra-assay comparison of LOD values for three targets using three separate singleplex linkage assays vs. one multiplex linkage assay.

| Target Protein | LOD singleplex Digital Affinity Linkage Assay pg/mL | LOD multiplex Digital Affinity Linkage Assay pg/mL |
|---|---|---|
| PSA | 5.1 | 2.5 |
| hEGF | 1.7 | 3.1 |
| IL-10 | 361 | 333 |

The results show that performing the assay in multiplex does not reduce sensitivity and results in comparable LOD values for each of the three targets when comparing to the singleplex assays.

All patents, patent applications, and other published reference materials cited in this specification are hereby incorporated herein by reference in their entirety.

What is claimed is:

1. A method of quantifying a target in a sample, the method comprising:
   contacting the sample with a first affinity agent linked to a solid support, wherein the first affinity agent specifically binds to the target, if present, thereby forming a target bound to the first affinity agent;
   separating the target bound to the first affinity agent from unbound material in the sample based on the presence or absence of the solid support, thereby generating a separated sample comprising the target bound to the first affinity agent;
   contacting the separated sample with a second affinity agent comprising a first label and a third affinity agent comprising a second label, wherein the first label is a first nucleic acid label and the second label is a second nucleic acid label that generates a signal that is distinguishable from a signal generated from the first nucleic acid label; and wherein the second and third affinity agents specifically bind to the target, thereby forming a target-labeled affinity agent complex;
   separating the target-labeled affinity agent complex from uncomplexed second and third affinity agents based on the presence or absence of the solid support, thereby generating a separated target-labeled affinity agent complex;
   partitioning at least the separated target-labeled affinity agent complex into a plurality of partitions; and
   detecting in the plurality of partitions a number of partitions above the number expected from random distribution that comprise the first and second labels in the same partition, thereby quantifying the target in the sample.

2. The method of claim 1, wherein the first and second nucleic acid labels are amplified following the partitioning.

3. The method of claim 2, wherein each of the first and second nucleic acid labels are detected using an intercalating dye or a DNA probe selected from the group consisting of a probe having a reporter on one end and a quencher on the other, a molecular beacon probe, a double-stranded probe, a dual hybridization probe, and a double-quenched probe.

4. The method of claim 3, wherein the first and second nucleic acid labels are detected using different signal levels of the same DNA probe or intercalating dye.

5. The method of claim 1, wherein the first and second labels are each linked to streptavidin and the second and third affinity agents are biotinylated, and wherein prior to a first step of the method the first and second streptavidin-linked labels are conjugated to the biotinylated first and second affinity agents, respectively, by streptavidin-biotin interaction.

6. The method of claim 1, wherein the first affinity agent is biotinylated and the solid support is linked to streptavidin, and wherein prior to a first step of the method the streptavidin-linked solid support is linked to the biotinylated first affinity agent by streptavidin-biotin interaction.

7. The method of claim 1, wherein the solid support or the plurality of solid supports are selected from the group consisting of magnetic beads and non-magnetic beads.

8. The method of claim 1, wherein the solid support or the plurality of solid supports comprise magnetic beads and the target-labeled affinity agent complex is separated from the uncomplexed components in the sample using a magnet that attracts the magnetic beads in the target-labeled affinity agent complex.

9. The method of claim 1, wherein the target is selected from the group consisting of a protein, a protein aggregate, and a protein oligomer.

10. The method of claim 1, wherein the target is a complex of two or more interacting proteins and the second and third affinity agents each bind to one of the interacting proteins in the complex and the method further comprises calculating a binding affinity ($K_D$) of the interacting partners.

11. The method of claim 1, wherein each of the first, second, and third affinity agents specifically binds to a different epitope on the target.

12. The method of claim 1, wherein the first, second, and third affinity agents are each selected from the group consisting of an antibody, an antibody fragment, and a nucleotide aptamer.

13. The method of claim 12, wherein the antibody is a monoclonal antibody and/or a polyclonal antibody.

14. The method of claim 1, wherein the partitions are droplets.

15. The method of claim 1, wherein the sample comprises a plurality of different targets, and wherein for each of the plurality of different targets in the sample, a set of first, second, and third affinity agents is provided wherein each of the first, second, and third affinity agents specifically binds to the target.

* * * * *